United States Patent [19]

VandenBerg

[11] Patent Number: Plant 7,324

[45] Date of Patent: Sep. 11, 1990

[54] CHRYSANTHEMUM PLANT NAMED ORINDA

[75] Inventor: Cornelis P. VandenBerg, Salinas, Calif.

[73] Assignee: Yoder Brothers, Inc., Barberton, Ohio

[21] Appl. No.: 337,463

[22] Filed: Apr. 13, 1989

[51] Int. Cl.[5] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Orinda particularly characterized by its flat capitulum form; spoon daisy capitulum type; white ray floret color; diameter across face of capitulum of up to 6 cm at maturity when grown as a pinched spray pot mum; uniform eight week photoperiodic flowering response to short days; medium plant height when grown as a pinched pot mum; and spreading branching pattern.

3 Drawing Sheets

The present invention comprises a new and distinct cultivar of Chrysanthemum, botanically known as *Dendranthema grandiflora,* and referred to by the cultivar name Orinda.

Orinda, identified as 84-Y67001, was originated from a cross made by Cornelis P. VandenBerg in a controlled breeding program in Salinas, Calif., in 1984.

The female parent of Orinda was an unnamed seedling, identified as 81-#02023. The male parent of Orinda was an unnamed seedling, identified as 82-H77012.

Orinda was discovered and selected as one flowering plant within the progeny of the stated cross by Cornelis P. VandenBerg in November of 1984, in a controlled environment in Salinas, Calif.

The first act of asexual reproduction of Orinda was accomplished when vegetative cuttings were taken from the initial selection in January of 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Orinda are firmly fixed and are retained through successive generations of asexual reproduction.

Orinda has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Orinda, which, in combination, distinguish this Chrysanthemum as a new and distinct cultivar:

1. Flat capitulum form.
2. Spoon daisy capitulum type.
3. White ray floret color.
4. Diameter across face of capitulum up to 6 cm at maturity when grown as a pinched spray pot mum.
5. Uniform eight week photoperiod flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum in a 15 cm pot.
7. Branching pattern is spreading.

The accompanying photographic drawings show typical inflorescence and leaf characteristics of Orinda, with the colors being as nearly true as possible with illustrations of this type. Sheet 1 is a color photograph of Orinda grown as a pinched spray pot mum grown in a 10 cm pot. Sheet 2 is a black and white photograph of three views of the inflorescence of Orinda. Sheet 3 is a black and white photograph showing the upper and under sides of the leaves of Orinda at three stages of development (mature, intermediate and immature).

Of the commercial cultivars known to the inventor, the most similar in comparison to Orinda is Spears, disclosed in U.S. Plant Pat. No. 5,620. Reference is made to attached Chart A, which compares certain characteristics of Orinda to the same characteristics of Spears.

Similar traits are ray floret color, capitulum form and type, branching pattern, plant height and flowering response period. Orinda has a smaller diameter across face of capitulum than Spears. In addition, flower placement of Orinda is more open and attractive than that of Spears, which often is clubby to very clubby.

In the following description color references are made to The Royal Horticultural Society Colour Chart. The clear white ray floret color of Orinda is not represented in the RHS Colour Chart. The color values were determined on plant material grown as a pinched spray pot mum grown in a 10 cm pot in Salinas, Calif. on Oct. 14, 1988.

Classification:

*Botanical.*—*Dendranthema grandiflora* cv Orinda.

*Commercial.*—Spoon daisy spray pot mum.

INFLORESCENCE

A. Capitulum:

*Form.*—Flat.

*Type.*—Spoon daisy.

*Diameter across face.*—Up to 6 cm at maturity.

B. Corolla of ray florets:

*Color (general tonality from a distance of three meters).*—White.

*Color (upper surface).*—White.

*Color (under surface).*—White.

*Shape.*—Base tubular. Distal portion open, flattened and spoon-like.

C. Corolla of disc florets:

*Color (mature).*—5A.

*Color (immature).*—144B to 144C.

D. Reproductive organs:

*Androecium.*—Present on disc florets only; no pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching pattern.*—Spreading.

B. Foliage:

*Color (upper surface).*—137A to 147A.

*Color (under surface).*—147B.

*Shape.*—Lobed and slightly serrated.

CHART A

COMPARISON OF ORINDA AND SPEARS

| Cultivar | Orinda | Spears |
|---|---|---|
| Ray Floret Color | White | White |
| Capitulum Form and Type | Flat Spoon Daisy | Flat Spoon Daisy |
| Branching Pattern | Spreading | Spreading |
| Diameter Across Face of Capitulum | Up to 6 cm | 7 to 8 cm |
| Plant Height | Medium | Medium |
| Flowering Response Period | 8 Weeks | 8 Weeks |

Comparisons Made of Plants Grown As Pinched Spray Pot Mums In Salinas, California

I claim:

1. A new and distinct Chrysanthemum plant named Orinda, as described and illustrated.

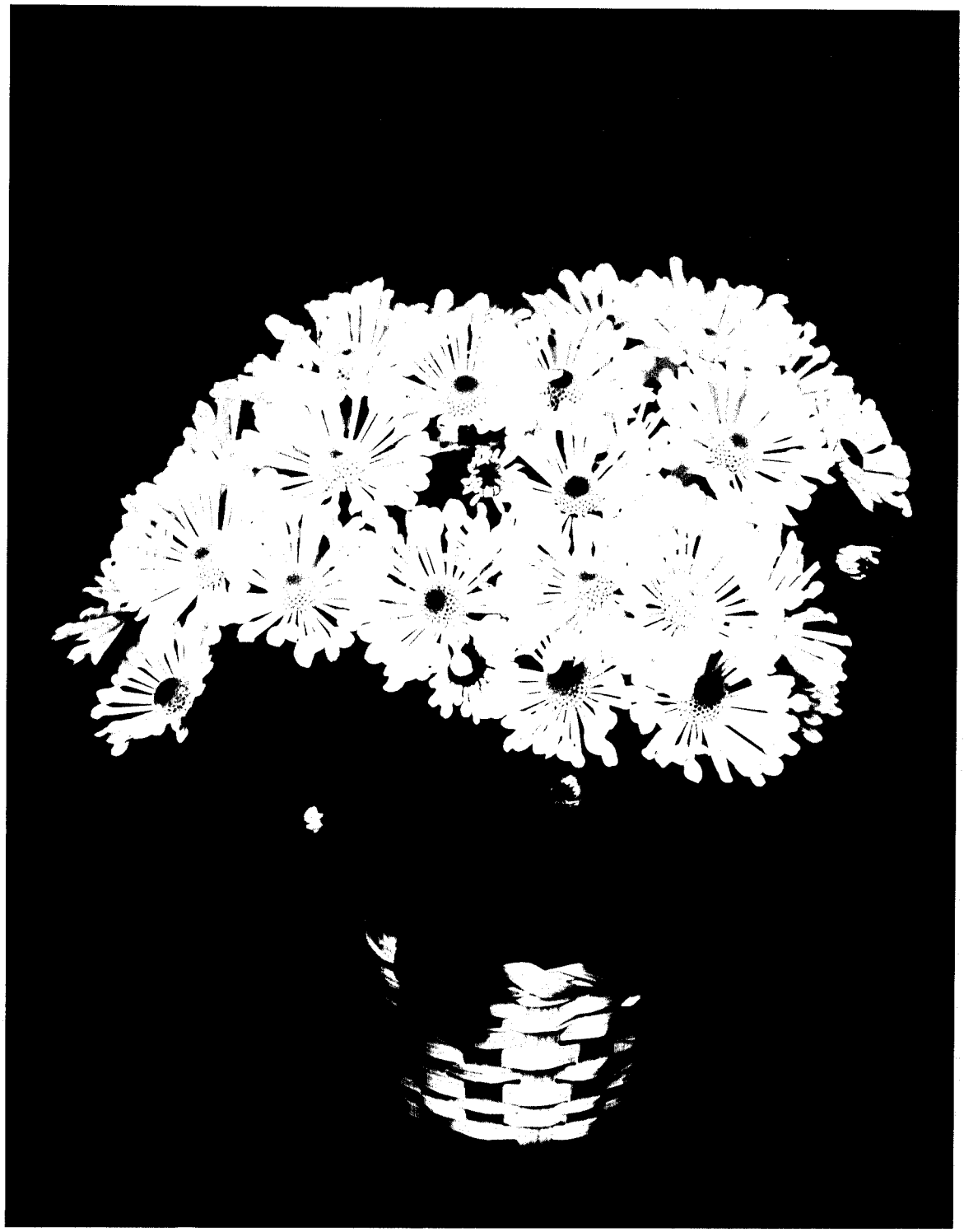

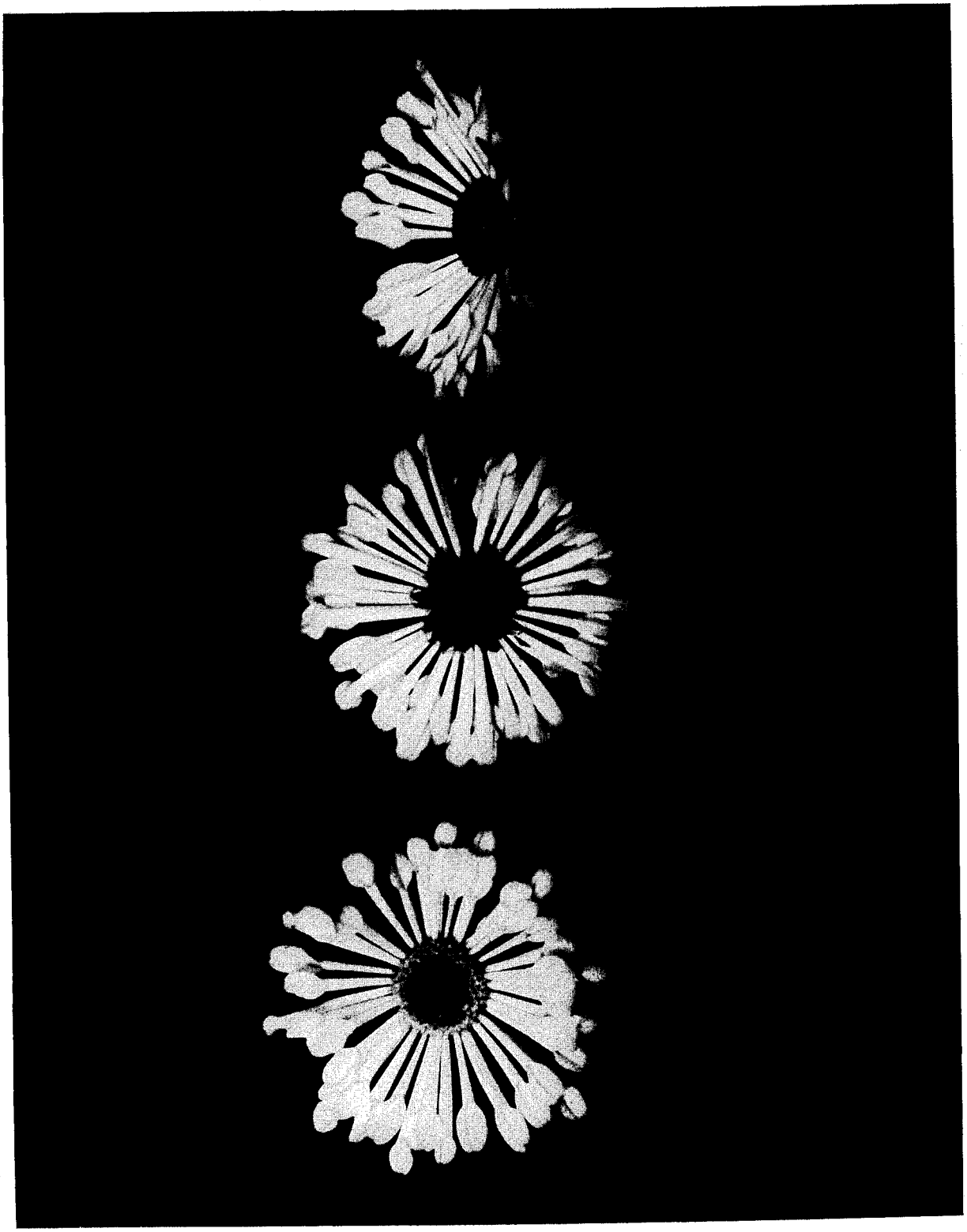

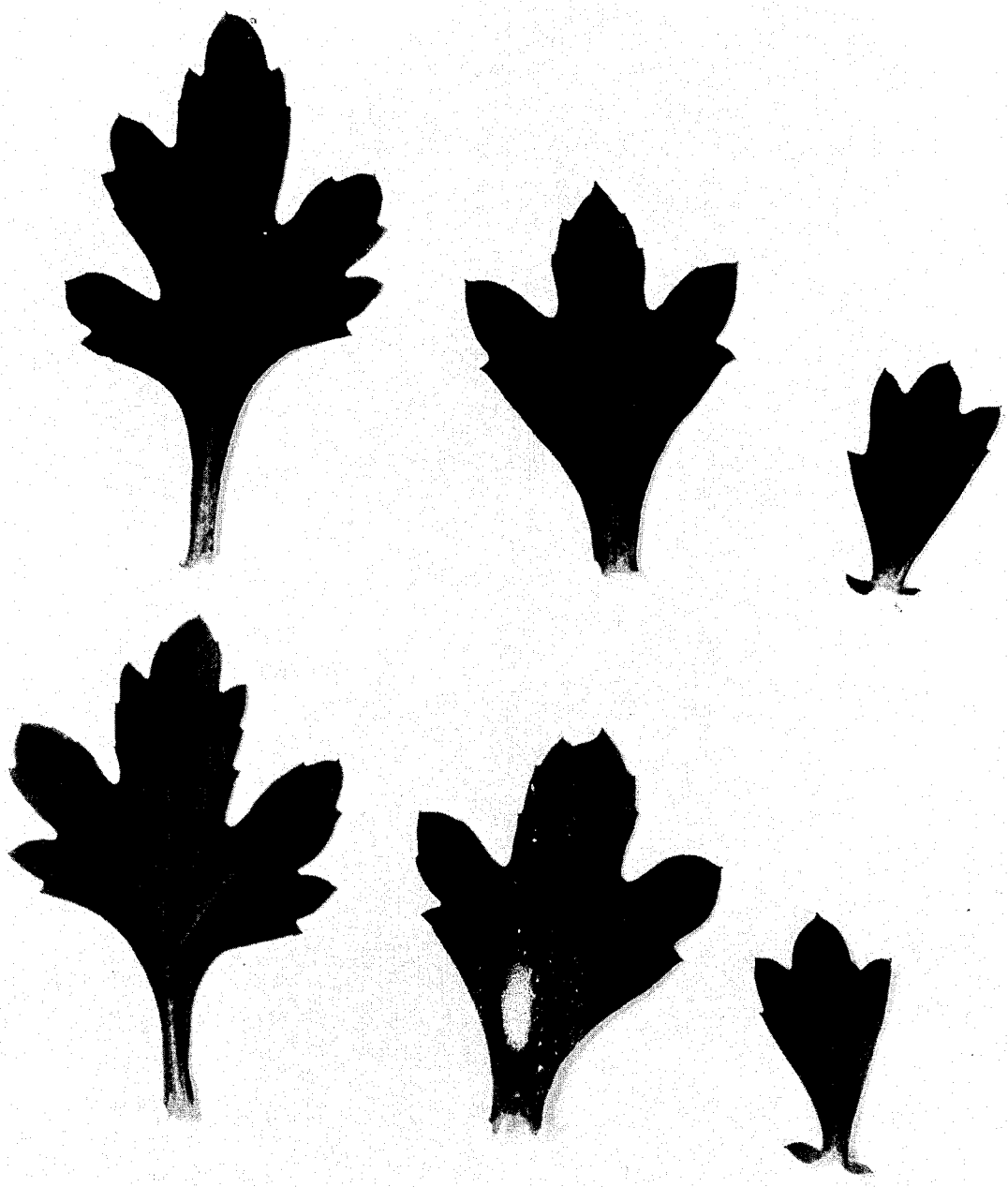

* * * * *